United States Patent
Halik et al.

(10) Patent No.: US 7,247,735 B2
(45) Date of Patent: Jul. 24, 2007

(54) OCTUPOLAR MOLECULES USED AS ORGANIC SEMICONDUCTORS

(75) Inventors: Marcus Halik, Erlangen (DE); Hagen Klauk, Erlangen (DE); Guenter Schmid, Gemhofen (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 11/041,632

(22) Filed: Jan. 24, 2005

(65) Prior Publication Data

US 2005/0179032 A1    Aug. 18, 2005

Related U.S. Application Data

(63) Continuation of application No. PCT/EP03/08157, filed on Jul. 24, 2003.

(30) Foreign Application Priority Data

Jul. 26, 2002    (DE) ................ 102 34 188

(51) Int. Cl.
| | |
|---|---|
| C07D 409/04 | (2006.01) |
| C07D 409/10 | (2006.01) |
| C07D 409/14 | (2006.01) |
| C07D 407/04 | (2006.01) |
| C07D 407/10 | (2006.01) |
| H01L 51/00 | (2006.01) |
| H01L 35/24 | (2006.01) |
| C07D 407/14 | (2006.01) |
| C07D 403/04 | (2006.01) |
| C07D 403/10 | (2006.01) |
| C07D 403/14 | (2006.01) |
| C07D 401/04 | (2006.01) |
| C07D 401/10 | (2006.01) |
| C07D 401/14 | (2006.01) |

(52) U.S. Cl. .................. 549/59; 549/60; 549/83; 549/448; 546/255; 546/257; 546/276.4; 546/279.7; 546/281.7; 548/518; 257/40

(58) Field of Classification Search ............ 549/59, 549/60, 83, 448; 546/255, 257, 276.4, 279.7, 546/281.7; 548/518
See application file for complete search history.

(56) References Cited

FOREIGN PATENT DOCUMENTS

| JP | 2001085713 | 3/2001 |
| JP | 2002322173 | 11/2002 |

OTHER PUBLICATIONS

Ponomarenko et al. Advanced Functional Materilas, 13(8): 591-596, 2003.*
International Search Report dated Mar. 26, 2004.
Bras et al., "Preparation of Conjugated Gels of Regioregular HT Sexi(3-*n*-octylthiophene) and Related Star Molecules," *Chemistry of Materials*, vol. 12, No. 8, pp. 2372-2384, Jul. 2000.
Cherioux et al., "Synthesis and Electrochemical Properties of New Star-Shaped Thiophene Oligomers and Their Polymers," *Chemical Communications*, p. 2225-2226, 1998.
Cherioux et al., "Synthesis and Characterisation of an Octupolar and New Molecular Octupoles with Off-Resonant Third Order Optical Nonlinearities," *Chemical Communications*, p. 2083-2084, 1999.
Cherioux et al., "Synthesis and Electrochemical Properties of Novel 1,3,5-Tris(oligothienyl)benzenes: A New Generation of 3D Reticulating Agents," *Advanced Functional Materials*, vol. 11, No. 4, pp. 305-309, Aug. 2001.
Jarre et al., "Synthese Und Reaktionen Von Symmetrisch Substitutuierten S-Triazinen Unter Hohem Druck," *Tetrahedron*, vol. 31, pp. 619-623, 1975.
Kotha et al., "A General and Simple Method for the Synthesis of Star-Shaped Thiophene Derivatives," *Synlett*, No. 10, pp. 1621-1623, 1999.
Sixou et al., "The Routes Towards Three-Dimensional Conducting Polymers: 2. Transport Properties of Fully Conjugated Gels of Poly(3-*n*-octylthiophene)," *POLYMER*, vol. 38, No. 7, pp. 1581-1587.
PCT International Preliminary Examination Report and Notification of Transmittal dated Apr. 8, 2005.

* cited by examiner

*Primary Examiner*—Venkataraman Balasubramanian
(74) *Attorney, Agent, or Firm*—Jenkins, Wilson, Taylor & Hunt, P.A.

(57) ABSTRACT

In the case of the materials according to the invention, the charge carrier mobility in the correspondingly prepared films is achieved if the molecules are composed in such a way that side chains—consisting of conjugated aromatic or heteroaromatic systems—are attached in direct conjugation to a central aromatic or heteroaromatic ring so that the total molecule acquires an octupolar structure. This octupolar structure permits an effective π-π interaction of the molecules with one another in a manner such that stacking of a plurality of molecules along an imaginary axis (central ring) can take place and various stacks from among these stacks can interact with one another by intermeshing of the side chains. The electronic properties of the materials are determined both by the arrangement of the molecules in a layer and by the molecular design. The type of side chains and of the central ring which is electronically coupled to the side chains and ideally reinforces the effects in comparison with side chains considered in isolation is important for this purpose.

15 Claims, 3 Drawing Sheets

FIG 1A

▨ aromatic or heteroaromatic side chain

FIG 1B

◄──► Possible channels for charge transport

⇔ Interactions of the various molecular fragments with one another

FIG 2

←—→ Possible channels for charge transfer

OCTUPOLAR MOLECULES USED AS ORGANIC SEMICONDUCTORS

RELATED APPLICATIONS

This application is a continuation of PCT patent application number PCT/EP2003/008157, filed Jul. 24, 2003, which claims priority to German patent application number 10234188.5, filed Jul. 26, 2002, the disclosures of each of which are incorporated herein by reference in their entirety.

TECHNICAL FIELD

The present invention relates to novel octupolar compounds and their preparation and use as organic semiconductors and in particular for organic field effect transistors.

BACKGROUND ART

The mobilities of charge carriers in organic semiconductors are at present not more than 1–2 $cm^2/Vs$. The maximum operating frequency of transistors and hence of the electronic switching is limited by the mobility of the charge carriers (holes or electrons). Although mobilities of the order of magnitude of $10^0$ $cm^2/Vs$ are sufficient for driver application in the production of TFT active matrix displays, high-frequency applications are generally excluded.

For technical reasons, wireless information transmission (RF-ID systems) can be effected only above a certain minimum frequency. In systems which are supplied directly from the alternating electromagnetic field and hence also have no independent voltage supply, the carrier frequencies 125 kHz and 13.56 MHz are widely used. Fields of use are identification and marking technology (smart cards, ident tags (bar code replacement), electronic postage stamps, etc.).

On the one hand, products which contain a silicon-based chip are too expensive for many applications. For example, a silicon-based ident tag is not suitable for marking foods (price, expiry date, etc.).

On the other hand, polymers or organic semiconductors have the potential that cheap printing techniques can be used for their structuring and application.

However, the mobilities of the charge carriers in these materials are too low for the applications discussed above.

Processes for applying the semiconducting molecules (for example pentacene, oligothiophenes) in a manner which is as ordered as possible, for example by vacuum sublimation, have been developed. Ordered deposition of the organic semiconductor leads to an increase in the crystallinity of the semiconductor material and, owing to an improved π—π overlap between the molecules or the side chains, reduces the energy barrier [1]. These are substantially molecules having a linear structure.

Substitution of the semiconducting molecular units by bulky groups leads to the formation of liquid crystalline-like domains in the deposition of the organic semiconductor from the liquid or gas phase [2].

In the area of polymers, synthesis processes in which as high a regioregularity as possible is achieved by the use of asymmetric monomers have been developed [3].

In [4], various octupolar oligothienyl compounds are described. However, these have only a relatively low charge carrier mobility, in order to enable them to be advantageously used as organic semiconductors and are for the most part irreversibly oxidizable or reducible.

Kotha et al., Synlett 1999, No. 10, 1621–1623, disclose octupolar molecules based on benzene having short thiophene side chains.

SUMMARY OF THE INVENTION

In this invention, novel compounds for uses as organic semiconductors are described. The molecular structure of these compounds permits high mobility of the charge carriers in correspondingly prepared films.

1. As disclosed herein, octupolar compounds of the following general formula are provided, the octupolar molecule being present in the form of stacks or molecular clusters:

in which X is CH or N;
in which Y is CH or N;
in which Z is O, S or N—R, in which R may be H, alkyl or aryl;
in which n is 2–6;
in which m is 0–6;
$R_1$ is n-alkyl, sec-alkyl, tert-alkyl, fluoroalkyl and/or perfluoroalkyl;
$R_2$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and/or perfluoroaryloxy;
$R_3$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and/or perfluoroaryloxy.

In a preferred embodiment of the invention, m is 0, so that the compound according to the invention is composed of a central benzene or triazine and five-membered unsaturated rings in the side chains.

It is furthermore preferred if n is 3–6. This is particularly preferred if m is 0.

If m is not 0, m is preferably 2–6, more preferably 3–6.

In a preferred embodiment, Z is S. This is the case both if m is 0 and if m is not 0. For Z=N—R and R=alkyl, R preferably has 1–18 C atoms, more preferably 2–8 C atoms. R may be n-alkyl, sec-alkyl, tert-alkyl and/or cycloalkyl, n-alkyl being preferred. Examples are methyl, ethyl, butyl, propyl, pentyl, hexyl, heptyl, octyl, nonyl or decyl, in each case preferably as n-alkyls.

According to the invention, X is CH or N. Both possibilities are equally suitable for the compounds of the present invention.

According to the invention, Y may likewise be CH or N, both possibilities being equally suitable according to the invention.

In the compounds according to the invention, the radical $R_1$ is present on the carbon atom neighboring the group Z. This is important in order for the compounds according to the invention to be stable and reversibly oxidizable and therefore to be more suitable for use as organic semiconductors.

If $R_1$ is n-alkyl, sec-alkyl, tert-alkyl, fluoroalkyl or perfluoroalkyl, the number of C atoms in the alkyl chain is preferably 1–18 C atoms, more preferably 2–8 carbon atoms.

The radicals according to the invention for $R_1$ can preferably be partly fluorinated or perfluorinated, i.e. completely fluorinated. Perfluorination is preferred. According to the invention, fluorination is to be understood as meaning that H atoms have been replaced by one or more fluorine radicals.

In a particularly preferred embodiment, $R_1$ is an n-alkyl, n-fluoroalkyl and/or n-perfluoroalkyl radical. Here, it is particularly preferred if $R_1$ has 1–18, preferably 2–8, carbon atoms. It is also particularly preferred if $R_1$ is an ethyl and/or hexyl radical. If $R_1$ is one of said alkyl, n-alkyl, fluoroalkyl, n-fluoroalkyl, perfluoroalkyl and/or n-perfluoroalkyl radicals, the compounds according to the invention are more stable and better reversibly oxidizable. With regard to the use for organic field effect transistors, particularly good results were obtained with such compounds. In these cases, the organization of the molecules after application to a substrate is presumably better, so that better charge carrier mobility is achieved. This is not the case, for example, if $R_1$ is H, halogen or S-alkyl; according to the invention, the radicals H, halogen or S-alkyl are therefore not provided for $R_1$.

With regard to the preferred embodiments, $R_2$ is defined as follows for n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and perfluoroaryloxy:

If $R_2$ is n-alkyl, sec-alkyl, tert-alkyl, O-alkyl (alkoxy), fluoroalkyl, perfluoroalkyl, alkynyl, alkylthiol or alkylnitrile, the number of C atoms in the alkyl chain is preferably 1–18 C atoms, more preferably 2–8 carbon atoms.

For $R_2$=cycloalkyl, cycloalkyl radicals having 4–6 C atoms are preferred, more preferably having 5–6 C atoms, which in each case may also be partly fluorinated or perfluorinated.

If $R_2$ is an aryl radical, O-aryl radical or S-aryl radical, six-membered aryl radicals, such as phenyl, thiophenyl or pyridyl radicals are preferred, which may also be partly fluorinated or perfluorinated. Regarding O-aryl and S-aryl, O-phenyl and S-phenyl are preferred, which may also be partly fluorinated or perfluorinated.

It is particularly preferable if $R_2$ is an H, alkyl, fluoroalkyl and/or perfluoroalkyl radical.

It is furthermore preferred if $R_2$ is an n-alkyl, n-fluoroalkyl and/or n-perfluoroalkyl radical.

In these cases, $R_2$ preferably has 1–18 carbon atoms, more preferably 2–8 carbon atoms.

For $R_2$=halogen, the halogen radical may be Cl, Br and/or I. Preferred halides are Br and I.

With regard to n-alkyl, sec-alkyl, tert-alkyl, cycloalkyl, fluoroalkyl, perfluoroalkyl, aryl, fluoroaryl, perfluoroalkyl, alkoxy, fluoroalkoxy, aryloxy, fluoroaryloxy, perfluoroalkoxy and perfluoroaryloxy, $R_3$ is defined in the same way as $R_2$, also with regard to the preferred embodiments of $R_1$. In a preferred embodiment, however, $R_3$ is H. In the present invention, on the basis of the present state of knowledge, the chemical nature of the radical $R_3$ is less critical than the radicals $R_1$ and $R_2$, in particular $R_1$.

For $R_3$=halogen, the halogen radical may be Cl, Br and/or I. Preferred halides are Br and I.

Particularly preferably, the radicals $R_2$ and/or $R_3$ are an H or a short-chain alkyl group, such as methyl and/or ethyl.

The following compounds have proven to be particularly preferred for the present invention:

1,3,5-Tris[5-(5''-ethyl)-2,2':5',2''-terthiophenyl]-benzene 1,3,5-Tris[5-(5'-hexyl)-2,2'-biphenyl]benzene

5

1,3,5-Tris[-(5'''-ethyl)-2,2':5',2'':5'',2'''-quart-thiophene]benzene

6

2,4,6-Tris[5-(5''-ethyl)-2,2':5',2''-terthiophenyl]-1,3,5-triazine 2,4,6-Tris[5-(5'-ethyl)-2,2'-biphenyl]-1,3,5-triazine The octopular molecules of the present invention are present in the form of stacks or molecular clusters. In this form, they can interact with one another intramolecularly and transfer charges with high mobility.

According to the present invention, it is possible to use, as organic semiconductors, compounds of the following formula, the octupolar molecules being present in the form of stacks or molecular clusters:

in which Y is CH or N;

in which Z is O, S or N—R, in which R may be H, alkyl or aryl;

in which n is 2–6;

in which m is 0–6;

$R_1$, is n-alkyl, sec-alkyl, tert-alkyl, fluoroalkyl and/or perfluoroalkyl;

$R_2$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and/or perfluoroaryloxy;

$R_3$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and/or perfluoroaryloxy.

Regarding further embodiments and preferred uses, the radicals X, Y, Z, n, m, $R_1$, $R_2$ and $R_3$ are defined as above.

Use both as p-semiconductors and as n-semiconductors is preferred. These compounds can preferably be used in transistors, preferably in field effect transistors.

The compounds according to the invention can be prepared by known processes, as described, for example, in reference [4] (triketolization and dehydration of three equivalents of acetyl-aromatic molecules with tetrachlorosilane/ethanol (1:1)), [5] (aryl-aryl coupling) and [6] (aryl-aryl coupling). Triazine compounds according to the invention can be prepared, for example, by nucleophilic substitution of the corresponding lithium salts with cyanuric chloride.

In the present invention, reference is made to the following figures.

DETAILED DESCRIPTION OF THE INVENTION

In the case of the materials according to the invention, the charge carrier mobility in the correspondingly prepared films is achieved if the molecules are composed in such a way that side chains—consisting of conjugated aromatic or heteroaromatic systems—are attached in direct conjugation to a central aromatic or heteroaromatic ring so that the total molecule acquires an octupolar structure. This octupolar structure permits an effective π—π interaction of the molecules with one another in a manner such that stacking of a plurality of molecules along an imaginary axis (central ring) can take place and various stacks from among these stacks can interact with one another by intermeshing of the side chains. The electronic properties of the materials are determined both by the arrangement of the molecules in a layer and by the molecular design. The type of side chains and of the central ring which is electronically coupled to the side chains and ideally reinforces the effects in comparison with side chains considered in isolation is important for this purpose.

The compounds of the present invention have various advantages:

1. The mobility of the charge carrier is considerably improved in relation to comparable side chains considered in isolation.
2. Owing to their structure, the materials are readily soluble in conventional solvents and are therefore suitable for economical application techniques, such as printing, coating, etc.
3. The materials can alternatively also be vaporized.
4. The synthesis of the materials is comparatively simple.
5. It is possible to prepare materials having a large structural variation.
6. Both p-semiconductors and n-semiconductors can be prepared.

The compounds of the present invention can be used as organic semiconductors, use as n- and p-semiconductors being possible. In particular, the compounds of the present invention can be used in electronic components, such as transistors, preferably field effect transistors. Particularly suitable potential applications are identification and marking chips in smart cards, and ident tags (as bar code replacement).

Figure 1A:
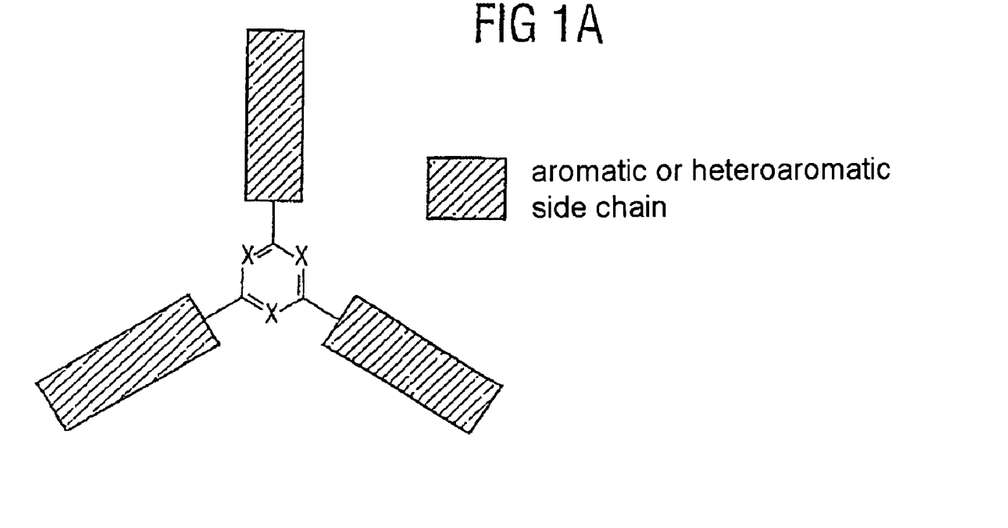
FIG. 1a schematically shows a compound according to the invention, in which the side chains are represented by rectangles.
Figure 1B:
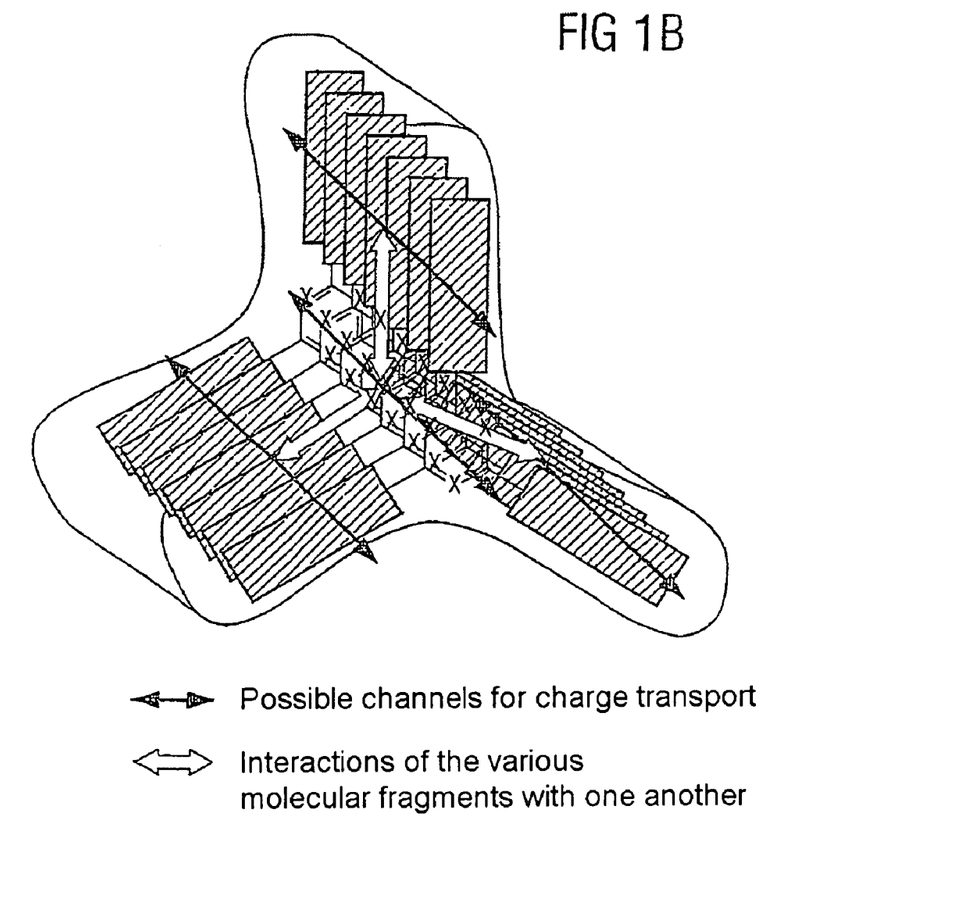
FIG. 1b schematically shows a stack of a plurality of the molecules shown in FIG. 1a and possible routes for intermolecular charge transport and intramolecular interaction routes between different molecular moieties.

The materials according to the invention are distinguished by a high mobility of the charge carriers in a correspondingly prepared film. This is due to the structure of the compounds according to the invention and their arrangement relative to one another in a layer, which ideally represents stacking of the molecules, the individual molecules interacting electronically with their neighbors in the stack (cf. FIG. 1b). This interaction is substantially more effective in the case of this class of molecule than in the case of comparable linear organic semiconductors, unless these have a monocrystalline structure. Furthermore, the electronic interaction of the individual molecular fragments (central ring, side chains) with one another ensures an enlargement of the π-system of the molecule, with the effect that high mobilities can be achieved with relatively short side chains, which can be obtained chemically substantially more simply and more economically, than with the molecules which are obtainable from a linear linkage of two comparable side chain fragments.

Figure 2:
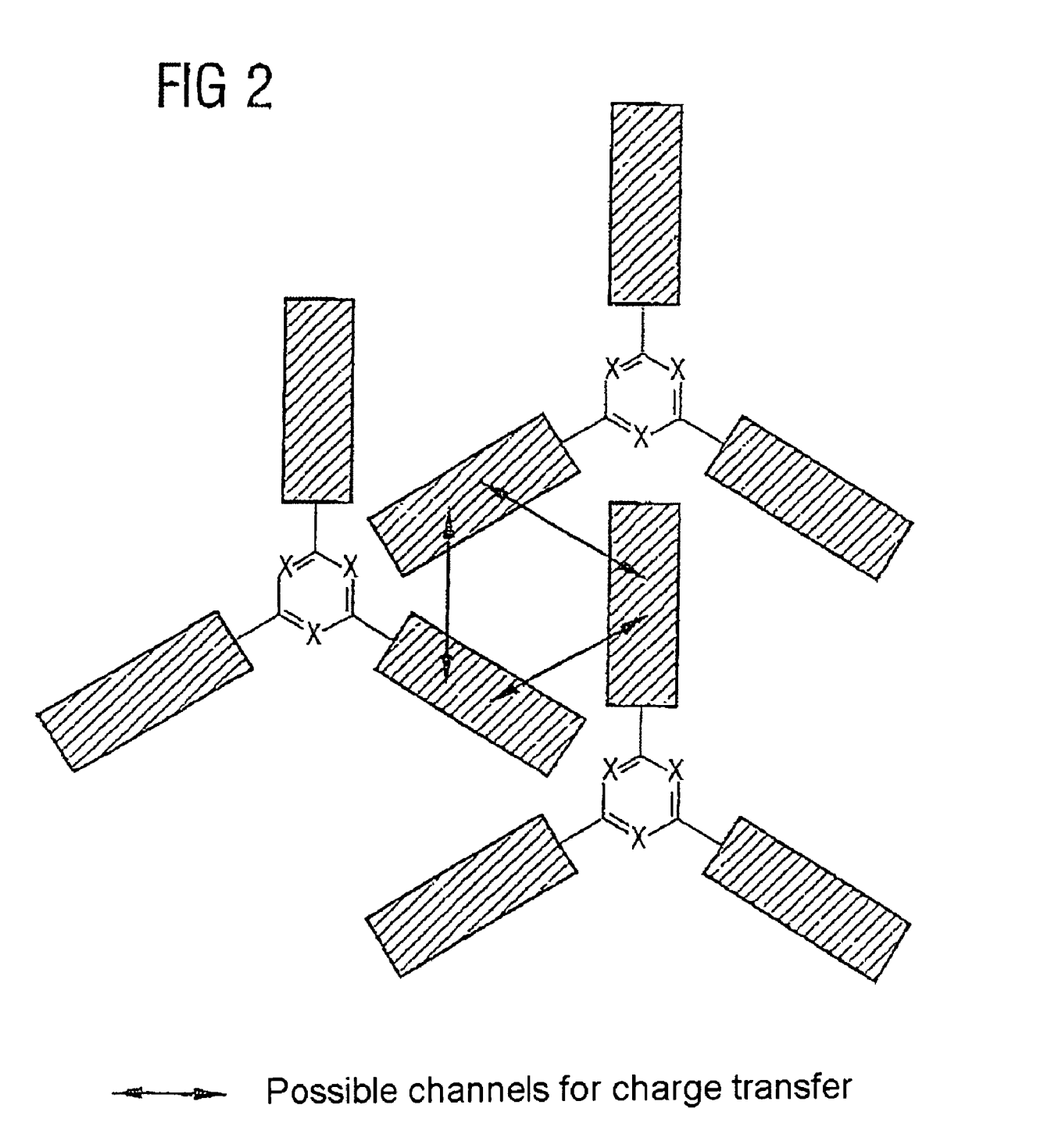
FIG. 2 schematically shows intermolecular interactions between different stacks of molecules.
Figure 3A:
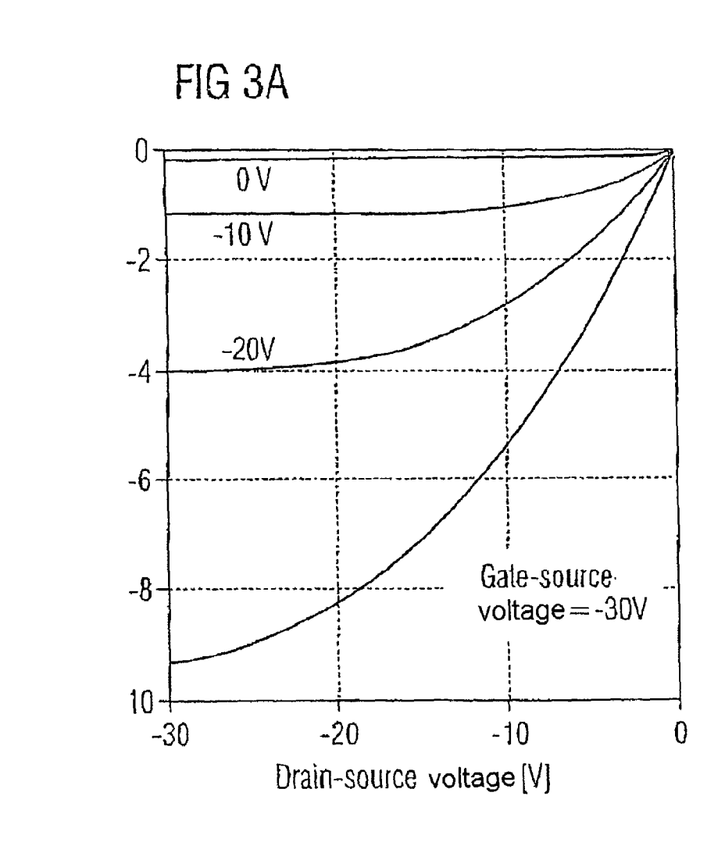
FIG. 3a shows a family of output characteristics of a transistor of the compound 4, processed according to example 9.
Figure 3B:
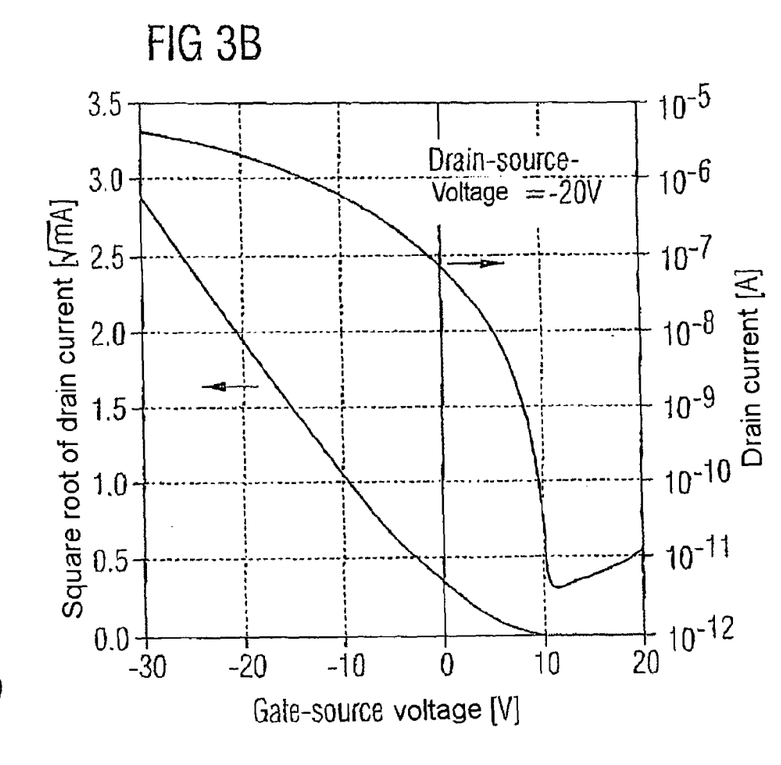
FIG. 3b shows transmission characteristics of a transistor of the compound 4, processed according to example 9.

The effective interaction of different stacks or molecular clusters with one another (intermeshing—FIG. 2) permits good charge transport by transmission of the charge from one stack to another. Thus, the charge transport can also be effected over relatively long distances (1–100 μm), as are usual as gate lengths in organic field effect transistors without direct conjugation by means of chemical bonding as in conjugated polymers being necessary.

The invention is explained in more detail below with reference to examples, which, however, do not limit the scope of the invention.

EXAMPLES

Example 1

1,3,5-Tris[5-(5''-ethyl)-2,2':5',2''-terthiophenyl]benzene (1)

Compound (1) can be prepared by at least two alternative routes:
a) Trimerization of 2-acetyl-(5''-ethyl)-2,2':5',2''-terthiophene by means of silicon tetrachloride in toluene/EtOH as a solvent, analogously to reference [4]
b) Aryl-aryl coupling of 1,3,5-tris[2-(5-bromo)-thiophenyl]benzene [4] with 2-tributylstannyl-(5'-ethyl)-2,2'-bithiophene by means of a Pd$^0$ catalyst in THF, analogously to reference [5].

In both cases, purification is effected by column chromatography over silica gel using n-hexane/CH$_2$Cl$_2$ (1:1) as an eluent (Rf=0.8) to give the same product.

$^1$H-NMR (CDCl3): δ [ppm]=1.33 (9H, t, CH$_3$); 2.83 (6H, q, CH$_2$); 6.70 (6H, dd, CH, J$_1$=3.5 Hz, J$_2$=1.1 Hz); 6.99 (6H, d, CH, J=3.6 Hz); 7.01 (6H, d, CH, J=4 Hz); 7.11 (6H, d, CH, J=4 Hz); 7.16 (6H, d, CH, J=3.6 Hz); 7.33 (6H, d, CH, J=4 Hz); 7.67 (3H, s, CH)

Example 2 (Comparative Example)

1,3,5-Tris[5-(2,2'-bithienyl)]benzene (2)

Compound (2) was prepared according to the literature method [4] and corresponds to one of the compounds disclosed there. The purification was effected by column chromatography using n-hexane/CH$_2$Cl$_2$ as an eluent (Rf=0.9). m.p.=135° C. (reference [4]=136° C.)

Example 3

1,3,5-Tris[5-(5'-hexyl)-2,2'-bithienyl]-benzene (3)

Compound (3) can be prepared by at least two alternative routes:
a) Trimerization of 2-acetyl-(5'-hexyl)-2,2'-bithiophene by means of silicon tetrachloride in toluene/EtOH as a solvent, analogously to reference [4]
b) Aryl-aryl coupling of 1,3,5-tris[2-(5-bromo)-thiophene]benzene [4] with 2-[(5-hexylthienyl)]magnesium bromide by means of an Ni$^{II}$ catalyst in THF, analogous to reference [6].

In both cases, the purification is effected by column chromatography over silica gel using n-hexane/CH$_2$Cl$_2$ (4:1) as an eluent (Rf=0.6) to give the same product.

$^1$H-NMR (CDCl3): δ [ppm]=0.88 (9H, t, CH$_3$); 1.30–1.36 (18H, m, CH$_2$); 1.66 (6H, tt, CH$_2$); 2.77 (6H, t, CH$_2$); 6.69 (6H, dd, CH, J$_1$=3.6 Hz, J$_2$=1.2 Hz); 7.04 (6H, d, J=3.8 Hz, CH), 7.18 (6H, d, J=3.9 Hz, CH), 7.23 (6H, d, J=3.9 Hz, CH); 7.31 (6H, d, J=3.8 Hz, CH); 7.69 (3H, s, CH).

Example 4

1,3,5-Tris[-(5'''-ethyl)-2,2':5',2'':5'',2'''-quartthiophenyl]benzene [4]

Compound (4) was by aryl-aryl coupling of 1,3,5-tris[2-(5-bromo)thiophenyl]benzene [4] with 2-tributylstannyl-(5''-ethyl)-2,2':5',2''-terthiophene by means of a Pd⁰ catalyst in THF, analogously to reference [5].

The purification is effected by column chromatography over silica gel using n-hexane/$CH_2Cl_2$ (1:1) as eluent (Rf=0.8).

$^1$H-NMR (CDCl3): δ [ppm]=1.35 (9H, t, $CH_3$); 2.84 (6H, q, $CH_2$); 6.81 (6H, dd, CH, $J_1$=3.4 Hz, $J_2$=1.2 Hz); 6.98 (6H, d, J=3.6 Hz), CH); 7.01 (6H, d, J=3.9 Hz, CH); 7.03 (6H, d, J=3.9 Hz, CH); 7.05 (6H, d, J=3.9 Hz, CH); 7.16 (6H, d, J=3.8 Hz, CH); 7.25 (6H, d, J=3.9 Hz, CH); 7.34 (6H, d, J=3.9 Hz, CH); 7.69 (3H, s, CH).

Example 5

2,4,6-Tris-[5-(5'-ethyl)-2,2'-bithienyl]-1,3,5-triazine (5)

Compound (5) was prepared by nucleophilic aromatic substitution of 2-[(5'-ethyl)-2,2'-bithienyl]lithium salt with cyanuric chloride in THF. The purification is effected by column chromatography over silica gel using n-hexane/$CH_2Cl_2$ (1:1) as an eluent (Rf=0.8).

Example 6

2,4,6-Tris-[5-(5''-ethyl)-2,2':5',2''-terthiophenyl]-1,3-triazine (6)

Compound (6) was prepared by nucleophilic aromatic substitution of 2-[(5''-ethyl)-2,2':5',2''-terthienyl]-lithium salt with cyanuric chloride in THF. The purification is effected by column chromatography over silica gel using n-hexane/$CH_2Cl_2$ (1:1) as an eluent (Rf=0.75).

Example 7

Preparation of a Substrate Solution

In principle, all organic solvents whose boiling point is lower than the decomposition temperature of the compounds 1–6 and in which these have a solubility of at least 0.1 percent by mass, e.g. chloroform, dichloromethane, THF, acetone, cyclohexanone, ethyl acetate, toluene, cresol, γ-butyrolactone, NMP and DMF, are suitable as solvents for the layer preparation.

100 mg of a compound described under examples 1–6 were dissolved in 10 g of chloroform by shaking the mixture of the two components in a closed sample tube on a mechanical shaker for 1 hour. The solution was then rendered particle-free by means of pressure filtration into a steam-cleaned sample tube (filter size 0.2 μm).

Example 8

Film Preparation (Spin Coating Technique)

A solution prepared as under example 7 was applied by spin coating (1000–5000 rpm, 20 s, nitrogen atmosphere) to a suitable substrate on which transistors and/or circuit structures had been defined beforehand (e.g. Si wafer, glass or flexible film). The substrate was then dried for 2 minutes at 80° C. under inert gas.

Example 9

Film Preparation (Vapor Deposition)

A compound (examples 1–6) was applied to a substrate, as under example 15, under a high vacuum ($10^{-6}$ to $10^{-7}$ mmHg) by means of an evaporator. Here, the vaporization times and substrate temperatures depended on the properties of the compounds and the desired layer thickness.

Example 10

Film Preparation (Printing)

A solution prepared as under example 7 and comprising corresponding additives is printed on a suitable substrate by means of a suitable screen in a screen printing machine and then dried at 80° C.

Example 11

Measurement of the Charge Carrier Mobilities

A field effect transistor processed as under examples 8–10 and consisting of gate electrode, gate dielectric and metal or polymer source and drain contacts is contacted on an analytical sampler by means of metal tips. Using an electrical parameter measuring apparatus (e.g. Agilent 4156), a transistor characteristic is measured. The charge carrier mobility is calculated from the characteristics. For compounds of examples 1–6, charge carrier mobilities are about $10^{-2}$ to more than $10^{-1}$ cm$^2$/Vs were determined and are shown in table 1.

TABLE 1

Charge carrier mobilities of examples 1–6.

| Compound | Film preparation | μ[cm$^2$/Vs] | Film preparation | μ[cm$^2$/Vs] |
|---|---|---|---|---|
| 1 | Ex. 8 | 0.04 | Ex. 9 | 0.3 |
| 2 | Ex. 8 | 0.0005 | Ex. 9 | 0.006 |
| 3 | Ex. 8 | 0.02 | Ex. 9 | 0.1 |
| 4 | Ex. 8 | 0.05 | Ex. 9 | 0.4 |
| 5 | Ex. 8 | 0.01 | Ex. 9 | 0.09 |
| 6 | Ex. 8 | 0.05 | Ex. 9 | 0.15 |

Table 1 shows that the charge carrier mobility of compound (2) is substantially lower than that of the compounds according to the invention. Moreover, it was observed that field effect transistors and other "devices" degrade within hours and have only low redox stability, whereas the field effect transistors and devices with the compounds according to the invention are stable for weeks.

Example 12

In order to demonstrate the suitability, according to the invention, of octupolar compounds where m is not equal to 0, the experiments described above for determining the charge carrier mobility were repeated on field effect transistors comprising the following model compounds, the film preparation having been effected according to example 9:

Dec-5T-dec (linear compound comprising decyl, 5 thiophene rings and decyl in this sequence):

Dec-2T-Ph-2T-dec (linear compound comprising decyl, 2 thiophene rings, phenyl, 2 thiophene rings, decyl in this sequence):

The following results were obtained:

| | μ [cm$^2$/Vs] |
|---|---|
| Dec-5T-dec: | 0.5 |
| Dec-2T-Ph-2T-dec: | 0.3 |

It was thus possible to show that, using conjugation via phenyl rings does not adversely affect the charge carrier mobility in transistors compared with corresponding compounds having a thiophene instead of the phenyl ring.

REFERENCES

[1] D. J. Gundlach, C. C. Kuo, S. F. Nelson and T. N. Jackson 57th Annual Device Research Conference Digest, pages 164–165, June 1999 H. E. Katz et al. Nature, Vol. 404, 2000, 478.
[2] P. Bäuerle et al, Synthetic Metals, 101, 1999, 544; Adv. Mater. 4, 1992, 102.
[3] Z Boa et al, Macromol. Symp. 2000, 1180. M. M. Bouman et al, Adv. Mater. 7, 1995, 385.
[4] F. Cherioux et al. Adv. Funct. Mater. Nov. 4, 2001, 305–309.
[5] H. E. Katz et al, Chem. Mater. 10, 1998, 457–459.
[6] R. D. McCullough et al, J. Org. Chem. 58, 1993, 904–912.

What is claimed is:

1. An octupolar compound of the following general formula, the octupolar molecule being present in the form of stacks or molecular clusters:

in which X is CH;
in which Y is CH or N;
in which Z is O, S or N—R, in which R may be H, alkyl or aryl;
in which n is 2–6;
in which m is 0;
$R_1$ is n-alkyl, sec-alkyl, tert-alkyl, fluoroalkyl and/or perfluoroalkyl;
$R_2$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and/or perfluoroaryloxy;
$R_3$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy and/or perfluoroaryloxy.

2. The compound as claimed in claim 1, wherein n=3–6.

3. The compound as claimed in claim 1, wherein Z is S.

4. The compound as claimed in claim 1, wherein R1 is an n-alkyl, n-fluoroalkyl and/or n-perfluoroalkyl radical.

5. The compound as claimed in claim 4, wherein R1 has 1–18 carbon atoms.

6. The compound as claimed in claim 1, wherein R2 is an H, alkyl, fluoroalkyl and/or perfluoroalkyl radical.

7. The compound as claimed in claim 1, wherein R2 is an n-alkyl, n-fluoroalkyl and/or n-perfluoroalkyl radical.

8. The compound as claimed in claim 1, wherein R2 has 1–18 carbon atoms.

9. The compound as claimed in claim 1, wherein the compound is selected from the group consisting of:

1,3,5-Tris[5-(5″-ethyl)-2,2′:5′,2″-terthiophenyl]benzene

1,3,5-Tris[5-(5′-hexyl)-2,2′-bithienyl]benzene and 1,3,5-Tris[-(5‴-ethyl)-2,2′:5′,2″:5″,2‴-quartthiophenyl]benzene 10. A method for preparing an organic semiconductor, the method comprising:
(a) providing a plurality of octupolar compounds of the following general formula:

in which X is CH;

in which Y is CH or N;

in which Z is O, S or N—R, in which R may be H, alkyl or aryl;

in which n is 2–6;

in which m is 0;

$R_1$ is n-alkyl, sec-alkyl, tert-alkyl, fluoroalkyl and/or perfluoroalkyl;

$R_2$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy, perfluoroaryloxy;

$R_3$ is H, halogen, n-alkyl, sec-alkyl, tert-alkyl, cycloalkyl, fluoroalkyl, perfluoroalkyl, aryl, fluoroaryl, perfluoroaryl, alkoxy, fluoroalkoxy, aryloxy, fluoroaryloxy, perfluoroalkoxy, perfluoroaryloxy; and (b) arranging the octupolar compounds as stacks or molecular clusters, whereby an organic semiconductor is prepared.

11. The method of claim 10, wherein the semiconductor is a p-semiconductor or an n-semiconductor.

12. The method of claim 10, wherein the semiconductor is in a transistor.

13. The method of claim 12, wherein the transistor is a in field effect transistor.

14. The compound as claimed in claim 5, wherein R1 has 2–8 carbon atoms.

15. The compound of claim 8, wherein R2 has 2–8 carbon atoms.

* * * * *